(12) United States Patent
Azuma et al.

(10) Patent No.: US 6,423,691 B1
(45) Date of Patent: Jul. 23, 2002

(54) PHARMACEUTICAL COMPOSITION FOR PROPHYLAXIS AND THERAPY OF DISEASES ASSOCIATED WITH OCULAR FUNDUS TISSUE CYTOGRAPHY

(75) Inventors: Mitsuyoshi Azuma, Nishinomiya; Yukuo Yoshida, Kobe; Yuji Sakamoto, Kobe; Jun Inoue, Kobe, all of (JP)

(73) Assignee: Senju Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/623,393

(22) PCT Filed: Mar. 3, 1999

(86) PCT No.: PCT/JP99/01031

§ 371 (c)(1),
(2), (4) Date: Sep. 5, 2000

(87) PCT Pub. No.: WO99/44624

PCT Pub. Date: Sep. 10, 1999

(30) Foreign Application Priority Data

Mar. 5, 1998 (JP) .............................. 10-53624

(51) Int. Cl.⁷ .............................. A61K 38/00
(52) U.S. Cl. .................... 514/19; 514/602; 514/604
(58) Field of Search .................. 514/602, 604, 514/19

(56) References Cited

FOREIGN PATENT DOCUMENTS

| EP | 0 504 938 A | 3/1992 |
| EP | 0 611 756 A | 2/1994 |
| EP | 0 623 627 A | 4/1994 |
| EP | 0 731 107 A | 2/1996 |
| EP | 0 771 565 A | 5/1997 |
| WO | WO 97/21690 | 11/1996 |
| WO | WO 98/50065 | 4/1998 |

OTHER PUBLICATIONS

"SJA6017, a newly synthesized peptide aldehyde inhibitor of calpain: amelioration of cataract in cultures rat lenses", Fukiage, C. et al., Biochimica et Biophysica Acta, 1361 (1997) 304–312.

"Inhibition of proteolysis protects hippocampal neurons from ischemia", Lee et al., Proc. Natl. Acad. Sci. USA, 88 (1991) 7233–7237.

"Protective effects of calpain inhibitors against neuronal damage caused by cytotoxic hypoxia in vitro and ischemia in vivo", Rami et al., Brain Research, 609 (1993) 67–70.

"Neuroprotection with a calpain inhibitor in a model of focal cerebral ischemia", Hong et al., Stroke, 25 (1994) 663–669.

"Spatial Resolution of fodrin proteolysis in postischemic brain", Saido et al., The Journal of Biological Chemistry, 268 (1993) 25239–25243.

Primary Examiner—James H. Reamer
(74) Attorney, Agent, or Firm—Wenderoth, Lind & Ponack, LLP

(57) ABSTRACT

A pharmaceutical composition for the prophylaxis and therapy of a disease arising from ocular fundus tissue cytopathy such as retinochoroidal disease, glaucoma, and posterior complication arising form photocoagulation, which contains, as an active ingredient, a compound of formula (I) wherein $R^1$ represents an alkyl group having 1 to 4 carbon atoms or an aryl group having 6 to 10 carbon atoms which is optionally substituted; $R^2$ and $R^3$ may be the same or different and each represents hydrogen or an alkyl group having 1 to 4 carbon atoms or $R^2$ and $R^3$ may jointly form a ring having 3 to 7 carbon atoms; and $R^4$ represents a lower alkyl group which substituted by aryl, cycloalkyl, or aromatic heterocyclic residue, or a pharmaceutically acceptable salt thereof.

18 Claims, 3 Drawing Sheets

PHARMACEUTICAL COMPOSITION FOR PROPHYLAXIS AND THERAPY OF DISEASES ASSOCIATED WITH OCULAR FUNDUS TISSUE CYTOGRAPHY

This is a 371 application of PCT/JP99/01031 filed Mar. 3, 1999.

TECHNICAL FIELD

The present invention relates to a drug for the prophylaxis and therapy of the diseases associated with ocular fundus tissue cytopathy.

BACKGROUND ART

The ocular fundus tissue comprises the retina, retinal vessels, retinal pigment epithelium, optic disc, choroid, and sclera and constitutes an organ for transmitting light stimuli from the crystalline lens to the brain through optic nerve cells. Therefore, injury of the ocular fundus tissue cells induces serious diseases leading to blindness in many cases. Impairment of ocular fundus tissue cells is frequently caused by ischemia and changes of various biological substances, such as elevation of excitatory amino acid levels and decreases in ATP. Moreover, the ocular fundus tissue cells are damaged by systemic diseases such as hypertension and diabetes, aging, and trauma as well. While laser photocoagulation is used for inhibition or elimination of neogenetic vessels in diabetic retinopathy and macular degeneration, elimination of vessel occlusion in retinal vessel occlusion, and the like, ocular fundus tissue cytopathy caused by changes in the circulation in the vicinity of the laser irradiation site, inflammatory reaction due to the heat of photocoagulation and the like poses problems.

The diseases associated with ocular fundus tissue injuries develop due to the various factors mentioned above or a complicated combination of various factors. The disease arising from injuries to the ocular fundus tissue includes retinochoroidal disease (e.g. retinal vascular abnormalities such as retinal vessel occlusion, retinal periphlebitis, Eales' disease, ischemic eye syndrome, retinal arteriolar macroaneurysm, etc.; retinopathy associated with hypertension or renal disease; diabetic retinopathy; retinal pigment epithelitis; retinal dystrophy; macular dystrophy; retinochoroidal atrophy; retinochoroiditis; macular degeneration; macular edema; retinal pigment epithelial detachment; retinal detachment; degenerative retinoschisis; tumors such as retinoblastoma, tumors of the retinal pigment epithelium, capillary hemangioma of the optic nerve head, etc.; optic neuropathies such as ischemic optic neuropathy etc.; optic disc swelling such as choked disc/papilledema etc.); and glaucoma associated with ocular fundus tissue cytopathy (e.g. open angle glaucoma, low tension glaucoma, angle closure glaucoma, etc.); and further the posterior complications arising from photocoagulation such as macular edema, retinal detachment, optic neuritis, abnormal visual field, abnormal light sense, and color vision defect. As used herein, by the posterior complications arising from photocoagulation is meant ocular fundus tissue cytopathy, caused by changes in the circulation in the vicinity of laser irradiation site, which is attributable to photocoagulation upon laser irradiation, inflammatory reaction due to the heat of photocoagulation, and diseases induced by these disorders.

As the current drug therapy of diseases associated with ocular fundus tissue cytopathy, microcirculation improving agents such as tocopherol nicotinate, which is a vitamin E preparation, pentoxifylline, etc., various steroidal drugs, antiprostaglandins, and antiphlogistic enzyme preparations are administered orally. However, those therapies are either not effective enough or have side-effect problems such as hypotension and gastrointestinal disorders. As therapeutic modalities for glaucoma, cholinergic agonists represented by pilocarpine, sympathomimetic drugs such as epinephrine, dipivefrin, etc., and β-adrenergic antagonists such as timolol, pindolol, carteolol, etc. are available for topical administration (e.g. eye-drops) but various side effects associated with their mechanisms of action are problems.

Recently, it has been reported that compounds having calpain inhibitory activity have an action to inhibit ischemic cell death [Lee K., Frank S., Vanderklish, P., Arai A., Lynch G., Proc. Natl. Acad. Sci., 88, 7233–7237 (1991), Rami A., Krieglstein J., Brain Res., 609, 67–70 (1993)]. However, those reports describe only the inhibitory effect on cell death in connection with the death of neurons in the hypocampus and do not indicate the inhibitory effect of the drugs on ocular fundus tissue cytopathy or their utility in the field of ophthalmology. Moreover, the inhibitors so far used have many shortcomings in the aspect of transfer to tissues and adverse reactions. EP0771565 states that a cysteine protease inhibitor is useful for neovascularization in diabetic retinopathy etc. but does not even hint at diseases associated with ocular fundus tissue cytopathy.

The present invention has for its object provision of a drug for the prophylaxis and therapy of ocular fundus tissue cytopathy, which overcomes the above-mentioned disadvantages. It is a further object of the present invention to provide a drug for the prophylaxis and therapy of diseases arising from ocular fundus tissue cytopathy and a method for the prevention and treatment of such diseases.

It should be understood that, in the context of the present invention, the term "ocular fundus tissue" means to include the retina, retinal blood vessels, retinal pigment epithelium, optic disc, choroid, sclera, and vitreous base, and that, of these tissues, the retina, retinal blood vessels, retinal pigment epithelium, optic disc, and choroid are sometimes referred to collectively as the retinochoroid.

DISCLOSURE OF THE INVENTION

The inventors of the present invention endeavored to develop a drug for the prophylaxis and therapy of ocular fundus tissue cytopathy, which is effective for improving ocular fundus tissue cytopathy and which is safe, and found that a compound of the following formula (I)

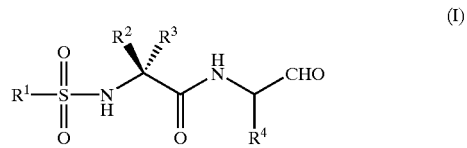

wherein $R^1$ represents an alkyl group having 1–4 carbon atoms or an aryl group having 6–10 carbon atoms which is optionally substituted; $R^2$ and $R^3$ may be the same or different and each represents hydrogen or an alkyl group having 1–4 carbon atoms or $R^2$ and $R^3$ may jointly form a ring having 3–7 carbon atoms; $R^4$ represents a lower alkyl group which is optionally substituted by aryl, cycloalkyl, or aromatic heterocyclic residue, and a pharmaceutically acceptable salt thereof exhibit remarkable prophylactic or therapeutic efficacy against ocular fundus tissue cytopathy.

BRIEF DESCRIPTION OF DRAWINGS

FIG. 3(a) and FIG. 3(b) are SDS electrophoretic images showing the cleavage product of endocellular spectrin obtained upon homogenation of retina tissues detected after incubation of rat retina tissues under hypoxia, wherein FIG. 3(a) and FIG. 3(b) show SDS electrophoretic images after incubation for 3 hours and 6 hours, respectively. In the Figures, M is a molecular weight marker, 1 shows retina tissues incubated in a glucose-containing culture medium in the presence of oxygen, 2 shows retina tissues incubated under hypoxia in a culture medium without glucose, 3 shows retina tissues incubated under hypoxia in a culture medium without glucose but supplemented with 100 μM of N-(4-fluorophenylsulfonyl)-L-valyl-L-leucinal (hereinafter abbreviated as Compound 1), and 4 shows retina tissues incubated under hypoxia in a culture medium without glucose but supplemented with 100 μM of Cbz-Val-Phe-H [hereinafter abbreviated as MDL]. Protein band of 220 kDa shows intact molecule of spectrin, and 145 and 150 kDa bands show the cleavage products of spectrin.

Figure 1:
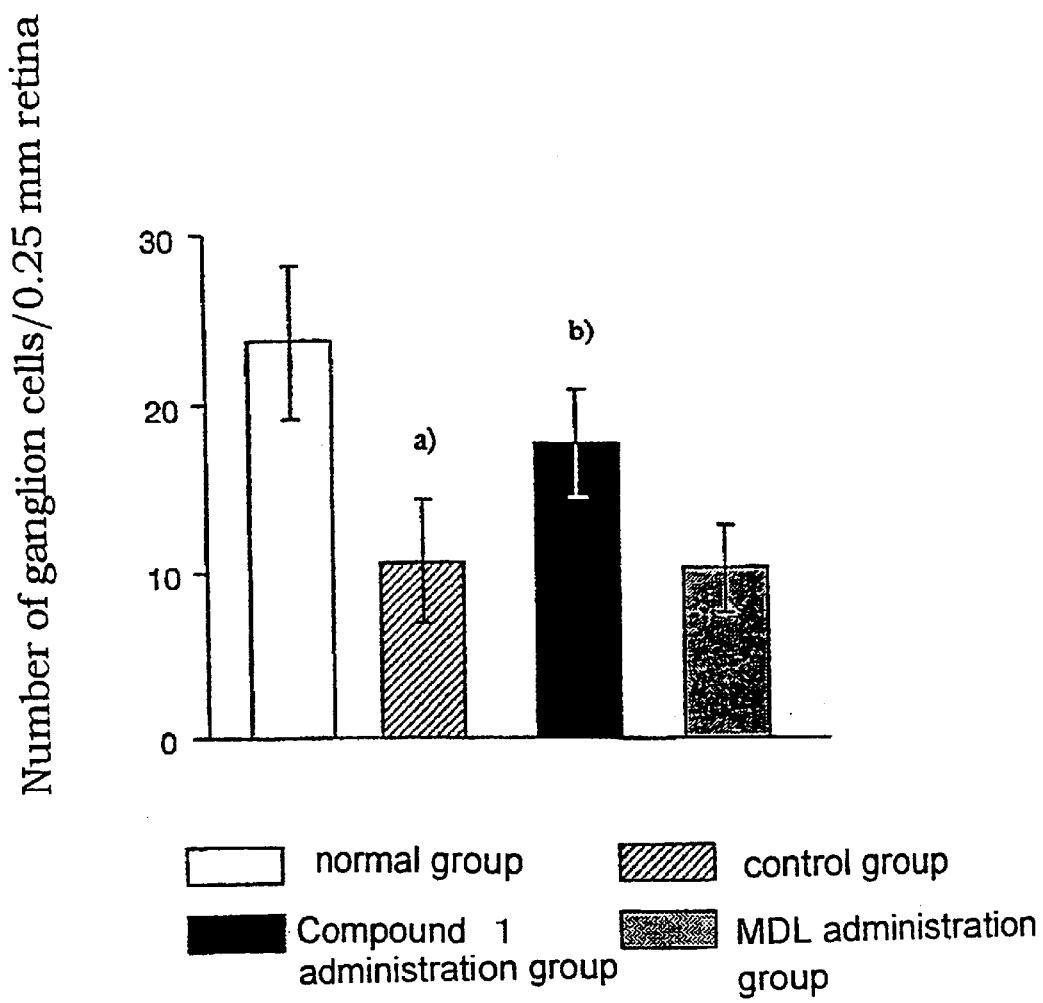
FIG. 1 is a diagrammatic representation of the effect on injury of rat retinal ganglion cells. The ordinate represents the number of ganglion cells. In the diagram, a) denotes a significant difference (p<0.01) from the normal group by Student's t-test; b) denotes a significant difference (p<0.01) from the control group by Student's t-test.

The compound of formula (I) for use in this invention and a pharmaceutically acceptable salt thereof are known compounds disclosed in Japanese Patent Unexamined Publication No. 43464/1997 (EP0771565) and can be produced typically by the processes described therein.

Referring to formula (I), when the amino acid moieties exist as optical isomers, they are L-isomers unless otherwise indicated.

Referring further to formula (I), the $C_1$–$C_4$ alkyl group for $R^1$ includes methyl, ethyl, propyl, isopropyl, butyl, isobutyl, sec-butyl, tert-butyl and the like. Of these, methyl is preferred.

The $C_6$–$C_{10}$ aryl group for $R^1$ includes phenyl, naphthyl, indenyl, azulenyl, and so forth. Preferred are phenyl and naphthyl.

The substituent group which may be present on the aryl group includes, for example, halogen (e.g., fluorine, chlorine, etc.), linear or branched $C_1$–$C_5$ alkyl (e.g., methyl, ethyl, propyl, isopropyl, butyl, isobutyl, sec-butyl, tert-butyl, pentyl, isopentyl, neopentyl, tert-pentyl and the like), trifluoromethyl, linear or branched $C_1$–$C_5$ alkoxy (e.g., methoxy, ethoxy, propoxy, isopropoxy, butoxy, isobutoxy, sec-butoxy, tert-butoxy, pentoxy, isopentoxy, neopentoxy, tert-pentoxy and the like), hydroxy, $C_2$–$C_5$ acyloxy (e.g., acetoxy, propionyloxy, butyryloxy, isobutyryloxy, valeryloxy and the like), carboxyl, and $C_2$–$C_5$ acyl (e.g., acetyl, propionyl, butyryl, isobutyryl, valeryl, isovaleryl, pivaroyl and the like). Preferred are halogen and $C_1$–$C_5$ alkyl. The more preferred are fluorine, chlorine, and methyl.

Preferred examples of the optionally substituted $C_6$–$C_{10}$ aryl group for $R^1$ are 4-fluorophenyl, 4-chlorophenyl, p-tolyl, and 2-naphthyl.

The linear or branched $C_1$–$C_4$ alkyl group mentioned for $R^2$ and $R^3$ includes methyl, ethyl, propyl, isopropyl, butyl, isobutyl, sec-butyl, tert-butyl and the like. Preferred are propyl, isopropyl, and tert-butyl. The more preferred is isopropyl.

Referring to $R^2$ and $R^3$, one of them is preferably hydrogen and the other is propyl, isopropyl, isobutyl, or tert-butyl. More preferably, $R^2$ is propyl, isopropyl, isobutyl, or tert-butyl and $R^3$ is hydrogen. Still more preferably, $R^2$ is isopropyl and $R^3$ is hydrogen.

The $C_3$–$C_7$ ring which may be formed jointly by $R^2$ and $R^3$ includes cyclopropylidene, cyclobutylidene, cyclopentylidene, cyclohexylidene, cycloheptylidene, and so forth. Cyclopentylidene and cyclohexylidene are particularly preferred.

The lower alkyl group mentioned for $R^4$ includes linear or branched groups having 1 to 6 carbon atoms, such as methyl, ethyl, propyl, isopropyl, butyl, isobutyl, sec-butyl, tert-butyl, pentyl, isopentyl, neopentyl, tert-pentyl, hexyl, 4-methylpentyl, 1,1-dimethylbutyl, 2,2-dimethylbutyl, 3,3-dimethylbutyl, 2-ethylbutyl and the like. Preferred are methyl and isobutyl. The above-mentioned lower alkyl group may be substituted by the following aryl group, cycloalkyl group, or aromatic heterocyclic residue.

The aryl group includes phenyl, 1-naphthyl, 2-naphthyl, and so forth. Particularly preferred is phenyl.

The cycloalkyl group preferably includes $C_3$–$C_6$ cycloalkyl; for example, cyclopropyl, cyclobutyl, cyclopentyl, cyclohexyl, and so forth. Particularly preferred is cyclohexyl.

The aromatic heterocyclic residue includes heteromonocyclic residues each containing at least one hetero atom selected from the group consisting of oxygen, nitrogen, and sulfur as a ring member and corresponding fused heterocyclic residues. The heteromonocyclic residue includes, but is not limited to, pyrrolyl, furyl, thienyl, oxazolyl, thiazolyl, imidazolyl, pyrazolyl, pyridyl and the like. The fused heterocyclic residue includes, but is not limited to, indolyl, quinolyl, benzothienyl, benzofuryl, indazolyl, quinazolinyl, phthalazinyl, quinoxalinyl and the like. Particularly preferred is indolyl.

Preferred examples of the lower alkyl group which may be substituted by aryl, cycloalkyl or aromatic heterocyclic residue as expressed by $R^4$ are isobutyl, benzyl, cyclohexylmethyl, and indol-3-ylmethyl.

Representative compounds of the formula (I) are

N-(2-naphthalenesulfonyl)-L-valyl-L-leucinal,

N-(4-fluorophenylsulfonyl)-L-valyl-L-leucinal,

N-(4-chlorophenylsulfonyl)-L-valyl-L-leucinal,

N-(4-methylphenylsulfonyl)-L-valyl-L-leucinal,

N-(4-fluorophenylsulfonyl)-L-valyl-L-phenylalaninal,

N-(2-naphthalenesulfonyl)-L-valyl-L-phenylalaninal,

N-(4-chlorophenylsulfonyl)-L-valyl-L-phenylalaninal,

N-(4-methylphenylsulfonyl)-L-valyl-L-phenylalaninal,

N-(4-chlorophenylsulfonyl)-L-valyl-L-tryptophanal,

N-(4-fluorophenylsulfonyl)-L-valyl-L-cyclohexylalaninal,

N-(2-naphthalenesulfonyl)-L-valyl-L-cyclohexylalaninal,

N-(4-chlorophenylsulfonyl)-L-valyl-L-cyclohexylalaninal, and pharmaceutically acceptable salts thereof.

Particularly preferred are

N-(4-fluorophenylsulfonyl)-L-valyl-L-leucinal, and a pharmacutically acceptable salt thereof.

The pharmaceutically acceptable salt of the compound of formula (I) includes salts with inorganic bases; for example, salts with alkali metals such as sodium, potassium, etc., salts with alkaline earth metals such as calcium, magnesium, etc., aluminum salt, ammonium salt, etc.; salts with organic bases such as trimethylamine, pyridine, picoline, ethanolamine, diethanolamine, triethanolamine, dicyclohexylamine, N,N-dibenzylethylenediamine, etc.; salts with inorganic acids such as hydrochloric acid, hydrobromic acid, nitric acid, sulfuric acid, phosphoric acid, etc.; salts with organic acids such as formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, etc.; and salts with amino acids such as arginine, lysine, ornithine, aspartic acid, glutamic acid, and so forth.

The prophylactic and therapeutic drug of the present invention can be optionally provided in any dosage form known in the art, that can be manufactured by a known pharmaceutical technology which comprises, for example, mixing or dissolving the active compound with a pharmaceutically acceptable carrier or vehicle. Of such dosage forms, the oral dosage form for use in humans include powders, granules, tablets, capsules, syrups, and other liquid preparations. Powders, granules, tablets and the like can be manufactured using optional pharmaceutically suitable carriers that are suitable for solid preparations, such as excipients (e.g., starch, glucose, fructose, sucrose, lactose, etc.), lubricants (e.g., magnesium stearate, calcium stearate, etc.), disintegrators (e.g., starch, crystalline cellulose, etc.), binders (e.g., starch, gum arabic, etc.), and so forth. Such solid preparation may be optionally coated with a coating agent (e.g., gelatin, sucrose, etc.) or an enteric coating (e.g., hydroxypropylmethylcellulose phthalate, methacrylic copolymers, shellac, etc.), so that the active compound may be released specifically in the bowels. For the manufacture of syrups and other liquids, various additives such as stabilizers (e.g., sodium edetate etc.), suspending agents (e.g., gum arabic, carmellose, etc.), corrigents (e.g., simple syrup, glucose, etc.), perfumes, etc. can be appropriately added. The dosage form for non-oral systemic administration includes injections, suppositories, etc. Injections can be manufactured by using solvents (e.g. water for injection, etc.), stabilizers (e.g., sodium edetate etc.), isotonizing agents (e.g., sodium chloride, glycerin, mannitol, etc.), pH control agents (e.g., hydrochloric acid, citric acid, sodium hydroxide, etc.), suspending agents (e.g., methylcellulose, sodium carboxymethylcellulose, etc.), and other suitable additives. For the manufacture of suppository, a suppository base (e.g., cacao butter, macrogol, etc.) and the like may be appropriately used. The dosage form for topical administration includes, for example, eye-drops and ophthalmic ointments. For the manufacture of eye-drops and ophthalmic ointments, a variety of known substances such as solvents (e.g., physiological saline, sterile purified water, etc.), stabilizers (e.g., sodium edetate, citric acid, etc.), emulsifiers (e.g., polyvinylpyrrolidone), suspending agents (e.g., hydroxypropylmethylcellulose, methylcellulose, hydroxymethylcellulose, etc.), surfactants (e.g., Polysorbate 80, hydrogenated polyethoxyethylene castor oil, etc.), preservatives (e.g., benzalkonium chloride, p-hydroxybenzoic esters, chlorobutanol, etc.), buffers (e.g., boric acid, borax (sodium borate), sodium acetate, citrate buffer, phosphate buffer, etc.), isotonizing agents (e.g., sodium chloride, glycerin, mannitol, etc.), pH control agents (e.g., hydrochloric acid, sodium hydroxide, etc.), and ointment bases (e.g., white petrolatum, lanolin, etc.) can be appropriately selected for use.

The prophylactic and therapeutic drug of the present invention is useful for the prevention and treatment of retinochoroidal diseases, glaucoma and ocular hypertension arising from ocular fundus tissue cytopathy, and posterior complications arising from photocoagulation. The retinochoroidal diseases include, but are not limited to, retinal vascular abnormalities such as retinal vessel occlusion, retinal periphlebitis, Eales' disease, ischemic eye syndrome, retinal arteriolar macroaneurysm, etc.; retinopathy associated with hypertension or renal disease; diabetic retinopathy; the retinal pigment epithelitis; retinal dystrophy; macular dystrophy; retinochoroidal atrophy; retinochoroiditis; macular degeneration; macular edema; retinal pigment epithelial detachment; retinal detachment; degenerative retinoschisis; tumors such as retinoblastoma, tumors of the retinal pigment epithelium, capillary hemangioma of the optic nerve head, etc.; optic neuropathies such as ischemic optic neuropathy etc.; and optic disc swelling such as choked disc/papilledema etc. The prophylactic and therapeutic drug of the present invention is particularly useful for the prevention and treatment of retinal vessel occlusion and macular degeneration. The glaucoma and ocular hypertension arising from ocular fundus tissue cytopathy include open angle glaucoma, low tension glaucoma, angle closure glaucoma, etc. and ocular hypertension with visual field defects. The prophylactic and therapeutic drug of the present invention is particularly useful for the prevention and treatment of low tension glaucoma. The posterior complications arising from photocoagulation include macular edema, retinal detachment, optic neuritis, abnormal visual field, abnormal light sense, or color vision defect.

The dosage of the compound of formula (I) or a pharmaceutically acceptable salt thereof according to the present invention is dependent on the target disease, clinical state and other conditions of patients, administration route, and other factors. Generally speaking, the objective effect can be achieved in a general dose of 1–1000 mg, preferably 10–500 mg, for oral administration, or generally 0.1–300 mg, preferably 1–150 mg, for parenteral administration. For topical administration, an eye-drop having a concentration of 0.001–1.0 w/v %, preferably 0.01–0.5 w/v %, can be instilled in the eye by 20–50 $\mu$l per dose, with a frequency of about 5–6 doses a day.

As long as the object of the present invention is not impaired, the prophylactic and therapeutic drug of the present invention can be used in combination with other active ingredients. As such other active ingredients, there can be mentioned anticoagulants such as warfarin potassium, urokinase, aspirin, etc.; vasoprotectants/hemostatics such as carbazochrome sodium sulfonate, etc.; peripheral vasodilators such as kallidinogenase, pentoxifylline, sarpogrelate hydrochloride, tocopherol nicotinate, etc., adrenocorticoids such as betamethasone, dexamethasone, prednizolone, etc., antiphologistic enzyme preparations such as serrapeptase, streptokinase, streptodornase, etc., antiglaucoma drugs such as $\beta$-blockers, mannitol, acetazolamide, etc., and antiprostaglandins.

EXAMPLE

The following examples and test examples are intended to illustrate the present invention in further detail and should by no means be construed as defining the scope of the invention. In the following examples and test examples, Compound 1 means N-(4-fluorophenylsulfonyl)-L-valyl-L-leucinal.

Example 1

| Tablets | |
|---|---|
| Compound 1 | 50 mg |
| Lactose | 80 mg |
| Starch | 17 mg |
| Magnesium stearate | 3 mg |
| Crystalline cellulose | 10 mg |

Tablets were prepared by a conventional method, which contained the above ingredients as materials for one tablet. The tablets may be applied with a conventional enteric coating (e.g., hydroxypropylmethylcellulose phthalate), a sugar coating, or a film (e.g., ethylcellulose), as necessary.

Example 2

| Capsules | |
|---|---|
| Compound 1 | 75 mg |
| Mannitol | 75 mg |
| Starch | 17 mg |
| Calcium stearate | 3 mg |

The above ingredients as materials for one capsule were homogeneously mixed, granulated by a conventional method, and filled into hard capsules. The granules may be applied with a conventional enteric coating (e.g., hydroxypropylmethylcellulose phthalate), a sugar coating, or a film (e.g., ethylcellulose), as necessary prior to filling.

Example 3

| Parenteral suspension | |
|---|---|
| Compound 1 | 750 mg |
| Sodium carboxymethylcellulose | 500 mg |
| Water for injection | to make 100 ml |

The above ingredients were aseptically admixed by a conventional method to provide a parenteral suspension.

Example 4

| Eye-drops | |
|---|---|
| Compound 1 | 50 mg |
| Boric acid | 700 mg |
| Borax | q.s. |
| Sodium chloride | 500 mg |
| Hydroxymethylcellulose | 0.5 g |
| Sodium edetate | 0.05 mg |
| Benzalkonium chloride | 0.005 mg |
| Sterile purified water | to make 100 ml |

Test Example 1

Effect on Rat Ocular Fundus Tissue Cytopathy Method:

Using male SD rats (b. wt. 150 g), the central retinal artery was occluded with an aneurysm clip under anesthesia with 5 w/v % ketamine HCl/2 w/v % xylazine HCl (3:1, 0.5 ml, i.p.) to arrest the blood flow for 75 minutes. In the normal group, the central retinal artery was exposed but ischemia was not introduced. Tissue specimens were prepared 5 days after reperfusion. For use as a tissue specimen, the enucleated eyeball was fixed in 4% formaldehyde and embedded in paraffin in a routine manner. Then, thin sections (3 $\mu$m thick) were prepared by transverse slicing at right angles with the retinal surface including the optic disc and stained with hematoxylin-eosin. Under the light microscope, the retinal neurons (ganglion cells) and inner nuclear layer cells were counted per 0.25 mm span of the retinal section at a predetermined distance (1–2 mm) from the optic disc. As the test drug, a parenteral suspension prepared as in Example 3 was administered intraperitoneally in a dose of 100 mg, as Compound 1, per kg body weight 15 minutes before arterial occlusion, immediately after reperfusion, and thereafter once daily (Compound 1 administration group). The control and normal groups were similarly given the vehicle used in Example 3. In the positive control group, Cbz-Val-Phe-H [S.C. Hong et al., Stroke, 25 (3), 663–669, 1994], 100 mg/kg, was similarly administered (MDL administration group).

Figure 2:
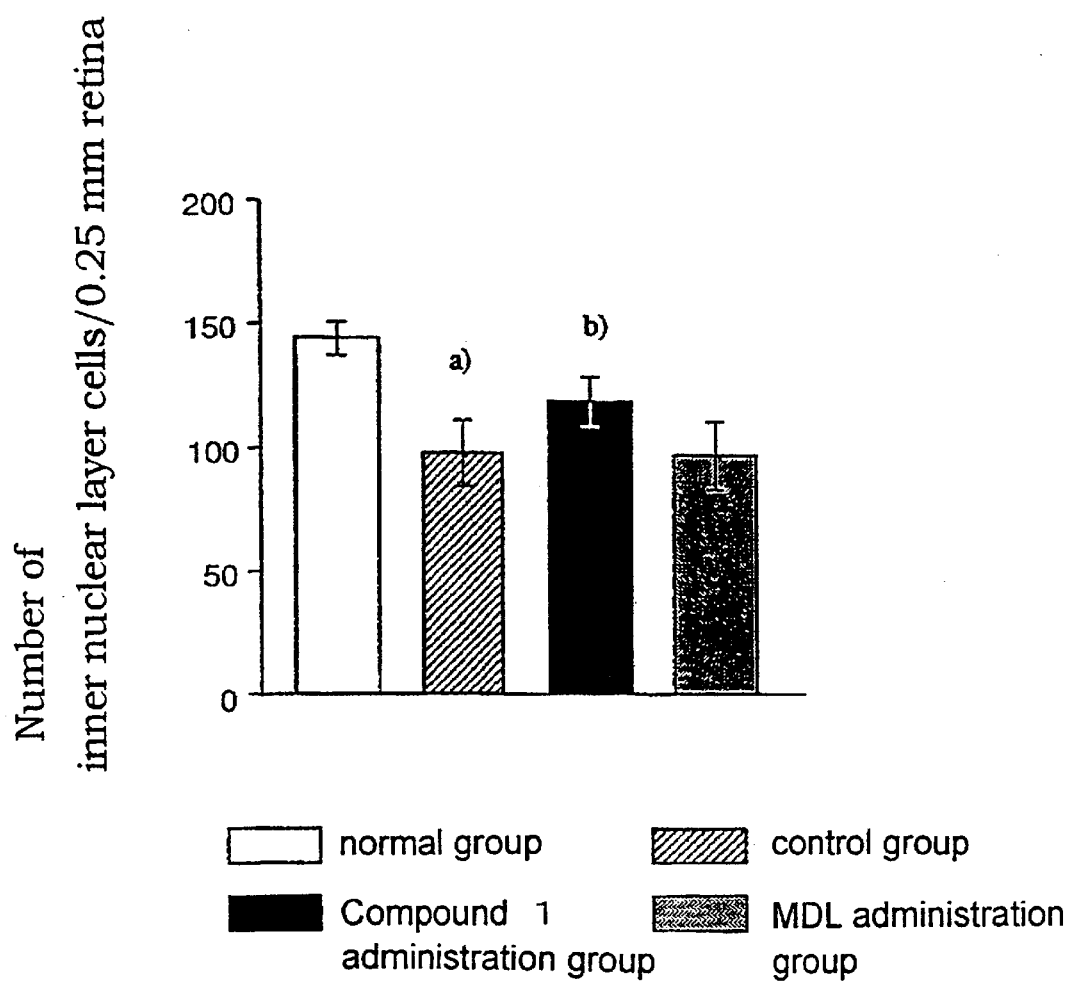
FIG. 2 is a diagrammatic representation of the effect on injury of the rat retinal inner nuclear layer cells. The ordinate represents the number of inner nuclear layer cells. In the diagram, a) denotes a significant difference (p<0.01) from the normal group by Student's t-test; b) denotes a significant difference (p<0.01) from the control group by Student's t-test.

Results:

The results are shown in FIGS. 1 and 2.

As compared with the normal group, both the ganglion cell count and inner nuclear layer cell count were significantly decreased by arterial occlusion. An administration of Compound 1 significantly inhibited the dereases in ganglion and inner nuclear layer cell counts caused by the arterial occlusion. In the MDL administration group, the degree of inhibition was slight.

The above results indicate that the active Compound 1 of the present invention is effective in improving ocular fundus tissue cytopathy.

Test Example 2

Effect on Rat Enucleated Retina Cytopathy Under Hypoxia

Method:

The ocular fundus tissue (retina) of male SD rats (b. wt. 150 g) was removed and incubated under hypoxia in RPMI 1640 medium (manufactured by (Gibco) without glucose. The ocular fundus tissue was homogenized 3 and 6 hours later, and the cleavage product of endocellular spectrin was isolated by SDS electrophoresis and detected using homophil prepared by the method of Saido et. al. [The Journal of Biological Chemistry, 268, 25239–25243 (1993)]. As the test compounds, Compound 1 and MDL were dissolved in ethanol to a concentration of 20 mM and added to the culture medium to a concentration of 100 $\mu$M (Compound 1 administration group and MDL administration group). As a control, the ocular fundus tissue of male SD rats (b. wt. 150 g) was incubated in the same manner in the presence of oxygen in RPMI 1640 medium containing glucose.

Figure 3A:
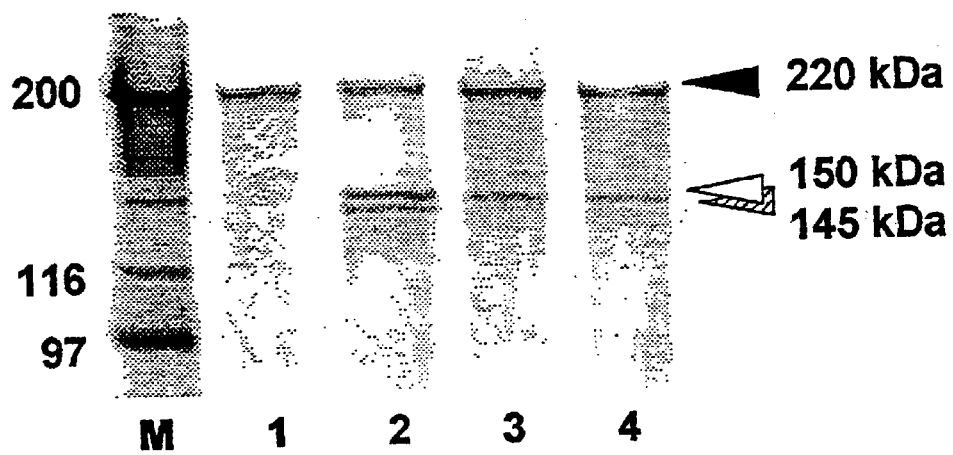
Figure 3B:
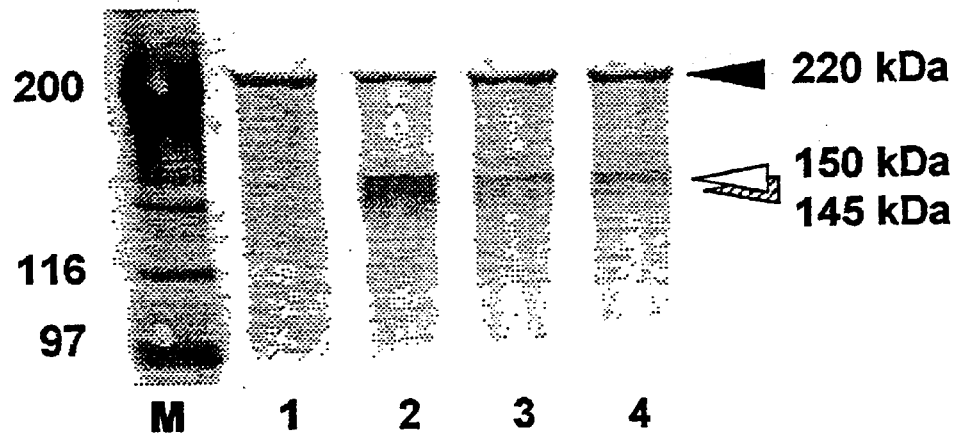

Results:

The results are shown in FIGS. 3(a) and 3(b).

When the tissue was incubated in a glucose-containing culture medium in the presence of oxygen, cleavage of spectrin was not observed. In contrast, when the tissue was incubated for 3 hours and 6 hours in a glucose-free culture medium under hypoxia, spectrin shown by a 220 kDa band was cleaved by calpain, which resulted in the detection of the cleavage products of spectrin as shown by 145 and 150 kDa bands. When the tissue was incubated in a culture medium supplemented with Compound 1 and MDL, which are calpain inhibitors, although a 150 kDa band due to the digestion of spectrin was somewhat detected, a 145 kDa band was not detected.

The foregoing results indicate elevation of calcium concentrations in the ocular fundus tissue due to the absence of oxygen, which leads to the activation of calpain, that is a calcium-dependent protease, and injury of the cells. The results clearly shows amelioration of the injury by Compound 1.

INDUSTRIAL APPLICABILITY

The prophylactic and therapeutic drug of the present invention is useful for the prevention and treatment of diseases arising from ocular fundus tissue cytopathy, e.g., retinal vascular abnormalities such as retinal vessel occlusion, retinal periphlebitis, Eales' disease, ischemic eye syndrome, retinal arteriolar macroaneurysm, etc.; retinopathy associated with hypertension or renal disease; diabetic retinopathy; retinal pigment epithelitis; retinal dystrophy; macular dystrophy; retinochoroidal atrophy; retinochoroiditis; macular degeneration; macular edema; retinal pigment epithelial detachment; retinal detachment; degenerative retinoschisis; tumors such as retinoblastoma, tumors of the retinal pigment epithelium, capillary hemangioma of the optic nerve head, etc.; optic neuropathies such as ischemic optic neuropathy etc.; optic disc swelling such as choked disc/papilledema etc.; glaucoma such as open angle glaucoma, low tension glaucoma, angle closure glaucoma; and ocular hypertension with visual field defects, posterior complications arising from photocoagulation such as macular edema, retinal detachment, optic neuritis, abnormal visual field, abnormal light sense, and color vision defect.

The present invention is based on Application No. 53624/1998 filed in Japan, the content of which is incorporated hereinto by reference.

What is claimed is:

1. A method for the prophylaxis or treatment of a disease arising from ocular fundus tissue cytopathy, which comprises administering an effective amount of a compound of the formula (I)

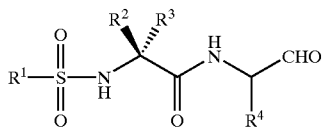

wherein $R^1$ represents an alkyl group having 1 to 4 carbon atoms or an aryl group having 6 to 10 carbon atoms which is optionally substituted; $R^2$ and $R^3$ may be the same or different and each represents hydrogen or an alkyl group having 1 to 4 carbon atoms or $R^2$ and $R^3$ may jointly form a ring having 3 to 7 carbon atoms; and $R^4$ represents a lower alkyl group which is optionally substituted by aryl, cycloalkyl, or aromatic heterocyclic residue, or a pharmaceutically acceptable salt thereof.

2. The method as claimed in claim 1, wherein $R^1$ in the formula (I) is phenyl or naphthyl, which may be substituted by fluorine, chlorine, or methyl.

3. The method as claimed in claim 1, wherein $R^1$ in the formula (I) is a group selected from the group consisting of methyl, 4-fluorophenyl, 4-chlorophenyl, p-tolyl, and 2-naphthyl.

4. The method as claimed in claim 1, wherein, in the formula (I), $R^2$ is propyl, isopropyl, or tert-butyl and $R^3$ is hydrogen.

5. The method as claimed in claim 1, wherein, in the formula (I), $R^2$ is isopropyl and $R^3$ is hydrogen.

6. The method as claimed in claim 1, wherein, in the formula (I), $R^4$ and $R^3$ jointly form cyclopentylidene or cyclohexylidene.

7. The method as claimed in claim 1, wherein, in the formula (I), $R^4$ is a group selected from the group consisting of isobutyl, benzyl, cyclohexylmethyl, and indol-3-ylmethyl.

8. The method as claimed in claim 1, wherein the compound is N-(4-fluorophenylsulfonyl)-L-valyl-L-leucinal or a pharmaceutically acceptable salt thereof.

9. The method as claimed in any of claim 1, wherein the disease arising from ocular fundus tissue cytopathy is a disease selected from the group consisting of retinochoroidal disease, glaucoma, and posterior complications arising from photocoagulation.

10. The method as claimed in to claim 9, wherein the disease arising from ocular fundus tissue cytopathy is retinochoroidal disease.

11. The method as claimed in claim 10, wherein the retinochoroidal disease is a member selected from the group consisting of retinal vessel occlusion, retinal periphlebitis, Eales' disease, ischemic eye syndrome, retinal arteriolar macroaneurysm, retinopathy associated with hypertension or renal disease, diabetic retinopathy, retinal pigment epithelitis, retinal dystrophy, macular dystrophy, retinochoroidal atrophy, retinochoroiditis, macular degeneration, macular edema, retinal pigment epithelial detachment, retinal detachment, degenerative retinoschisis, retinoblastoma, tumors of the retinal pigment epithelium, capillary hemangioma of the optic nerve head, ischemic optic neuropathy, and choked disc/papilledema.

12. The method as claimed in claim 11 wherein the retinochoroidal disease is retinal vessel occlusion.

13. The method as claimed in claim 11, wherein the retinochoroidal disease is macular degeneration.

14. The method as claimed in to claim 9 wherein the disease arising from ocular fundus tissue cytopathy is a posterior complication arising from photocoagulation.

15. The method as claimed in claim 14, wherein the posterior complication arising from photocoagulation is a member selected from the group consisting of macular edema, retinal detachment, optic neuritis, abnomal visual field, abnormal light sense, and color vision defect.

16. The method as claimed in to claim 9, wherein the disease arising from ocular fundus tissue cytopathy is glaucoma.

17. The method as claimed in claim 16, wherein the glaucoma is a member selected from the group consisting of open angle glaucoma, low tension glaucoma, and angle closure glaucoma.

18. The method as claimed in claim 17, wherein the glaucoma is low tension glaucoma.

* * * * *

UNITED STATES PATENT AND TRADEMARK OFFICE
CERTIFICATE OF CORRECTION

PATENT NO.    : 6,423,691 B1                                              Page 1 of 1
DATED         : July 23, 2002
INVENTOR(S)   : Mitsuyoshi Azuma et al.

It is certified that error appears in the above-identified patent and that said Letters Patent is hereby corrected as shown below:

<u>Title page,</u>
Item [54], change "CYTOGRAPHY" to -- CYTOPATHY --.

Item [56], FOREIGN PATENT DOCUMENTS, the two WO references, please delete second occurrence of "WO".

<u>Column 10,</u>
Line 14, please delete "any of".
Lines 20, 41 and 49, please delete "to".

Signed and Sealed this

Fifteenth Day of April, 2003

JAMES E. ROGAN
*Director of the United States Patent and Trademark Office*